US010517731B2

(12) United States Patent
Vunjak-Novakovic et al.

(10) Patent No.: US 10,517,731 B2
(45) Date of Patent: Dec. 31, 2019

(54) TISSUE ENGINEERING SYSTEM FOR MAKING PERSONALIZED BONE GRAFT

(71) Applicant: THE TRUSTEES OF COLUMBIA UNIVERSITY IN THE CITY OF NEW YORK, New York, NY (US)

(72) Inventors: Gordana Vunjak-Novakovic, New York, NY (US); Warren Grayson, New York, NY (US); Keith Yeager, Jersey City, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/633,317

(22) Filed: Jun. 26, 2017

(65) Prior Publication Data
US 2017/0290665 A1 Oct. 12, 2017

Related U.S. Application Data

(62) Division of application No. 13/148,735, filed as application No. PCT/US2010/026120 on Mar. 3, 2010, now Pat. No. 9,687,348.

(60) Provisional application No. 61/157,019, filed on Mar. 3, 2009, provisional application No. 61/249,999, filed on Oct. 9, 2009, provisional application No. 61/250,166, filed on Oct. 9, 2009.

(51) Int. Cl.
C12M 3/00 (2006.01)
A61F 2/28 (2006.01)
A61F 2/30 (2006.01)
C12M 1/12 (2006.01)
C12M 1/00 (2006.01)

(52) U.S. Cl.
CPC ............ *A61F 2/28* (2013.01); *A61F 2/3099* (2013.01); *A61F 2/30942* (2013.01); *C12M 21/08* (2013.01); *C12M 25/14* (2013.01); *C12M 29/10* (2013.01); *A61F 2002/30957* (2013.01)

(58) Field of Classification Search
CPC ...... A61F 2/28; A61F 2/30942; A61F 2/3099; A61F 2002/30957; C12M 21/08; C12M 25/14; C12M 29/10
See application file for complete search history.

(56) References Cited

U.S. PATENT DOCUMENTS

| 6,030,358 | A | 2/2000 | Odland |
| 6,197,575 | B1 | 3/2001 | Griffith et al. |
| 6,294,041 | B1 | 9/2001 | Boyce et al. |
| 6,372,257 | B1 | 4/2002 | Marchosky |
| 6,544,788 | B2 | 4/2003 | Singh |
| 6,632,651 | B1 | 10/2003 | Nevo et al. |
| 7,195,394 | B2 | 3/2007 | Vijay |
| 7,629,167 | B2 | 12/2009 | Geoffrey et al. |
| 7,635,586 | B2 | 12/2009 | Eugene |
| 7,738,682 | B2 | 6/2010 | Albert et al. |
| 7,819,934 | B2 | 10/2010 | Parrish et al. |
| 8,298,054 | B2 | 10/2012 | Geoffrey et al. |
| 8,367,410 | B2 | 2/2013 | Milica et al. |
| 8,381,780 | B2 | 2/2013 | Michael et al. |
| 8,468,871 | B2 | 6/2013 | Radislav et al. |
| 8,492,135 | B2 | 7/2013 | Damian et al. |
| 8,608,801 | B2 | 12/2013 | Clark et al. |
| 2002/0059049 | A1* | 5/2002 | Bradbury ............... G16H 50/50 703/11 |
| 2002/0110905 | A1 | 8/2002 | Barbera-Guillem et al. |
| 2002/0171178 | A1 | 11/2002 | Dean et al. |
| 2003/0006534 | A1 | 1/2003 | Taboas et al. |
| 2003/0161816 | A1 | 8/2003 | Fraser et al. |
| 2004/0091459 | A1 | 5/2004 | Nimni |
| 2004/0219659 | A1 | 11/2004 | Gregory et al. |
| 2005/0002910 | A1 | 1/2005 | Wolfinbarger et al. |
| 2006/0141623 | A1* | 6/2006 | Smith .................... C12M 21/08 435/383 |
| 2007/0233272 | A1 | 10/2007 | Boyce et al. |
| 2007/0276501 | A1* | 11/2007 | Betz ..................... A61F 2/30942 623/17.16 |

(Continued)

FOREIGN PATENT DOCUMENTS

EP 1359214 11/2003
WO WO2003093408 A1 * 11/2003

(Continued)

OTHER PUBLICATIONS

Grayson et al. "Effects of Initial Seeding Density and Fluid Perfusion Rate on Formation of Tissue-Engineered Bone." Tissue Eng Part A. Nov. 2008; 14(11): 1809-1820. (Year: 2008).*
Bancroft, et al., "Fluid flow increases mineralized matrix deposition in 3D perfusion culture of marrow stromal osteoblasts in a dose-dependent manner", Proc Natl Acad Sci U S A; 99(20):, Oct. 1, 2002, 12600-12605 pages.
Bhumiratana, et al., "Controlling Tissue Matrix Assembly of Human Mesenchymal Stem Cells Toward Engineering Native-Like Bone, Cartilage, and Osteochondral Grafts", Columbia University, 2012, 67 pages.
Braccini, et al., "Three-dimensional perfusion culture of human bone marrow cells and generation of osteoinductive grafts", Stem Cells, vol. 23, Issue 8, Sep. 2005, 1066-1072 pages.

(Continued)

*Primary Examiner* — Titilayo Moloye
(74) *Attorney, Agent, or Firm* — Ballast IP Law, LLP

(57) ABSTRACT

An anatomically-shaped, human bone graft may be cultivated ex vivo using a bioreactor capable of perfusing large complex porous scaffolds. Scaffolds derived from image-based modeling of a target are seeded with human mesenchymal stem cells and cultivated. A bioreactor configured to house complex three-dimensional scaffold geometries provides controlled flow for perfusion of the cells. Dense uniform cellular growth can be attained throughout the entire scaffold as a result of the medium perfusion. In an embodiment, the bioreactor has a mold into which perfusion medium is pumped under pressure and multiple ports through which the medium exits the mold.

19 Claims, 16 Drawing Sheets

(56) References Cited

U.S. PATENT DOCUMENTS

| | | | |
|---|---|---|---|
| 2008/0033572 A1* | 2/2008 | D'Antonio | A61K 35/32 623/23.51 |
| 2008/0113426 A1 | 5/2008 | Smith et al. | |
| 2009/0035856 A1 | 2/2009 | Parrish et al. | |
| 2009/0298173 A1 | 12/2009 | Ueda et al. | |
| 2010/0128961 A1 | 5/2010 | Geert | |
| 2011/0136225 A1 | 6/2011 | Vunjak-Novakovic et al. | |
| 2011/0151551 A1 | 6/2011 | Shujian et al. | |
| 2011/0151552 A1 | 6/2011 | Tieying et al. | |
| 2011/0202142 A1* | 8/2011 | Mao | A61L 27/3817 623/23.72 |
| 2011/0212500 A1 | 9/2011 | Steven et al. | |
| 2012/0003185 A1 | 1/2012 | Shai | |
| 2012/0028234 A1 | 2/2012 | Patrick et al. | |
| 2012/0035742 A1 | 2/2012 | Vunjak-Novakovic et al. | |
| 2012/0122220 A1 | 5/2012 | Shoshana et al. | |
| 2012/0206155 A1 | 8/2012 | Hua et al. | |
| 2013/0017131 A1 | 1/2013 | Parrish et al. | |
| 2013/0089925 A1 | 4/2013 | Richard et al. | |
| 2013/0274929 A1 | 10/2013 | Geoffrey et al. | |
| 2014/0106403 A1 | 4/2014 | Patrick et al. | |

FOREIGN PATENT DOCUMENTS

| | | |
|---|---|---|
| WO | 2005116186 | 12/2005 |
| WO | 2010102059 | 9/2010 |

OTHER PUBLICATIONS

Cao, et al., "Transplantation of chondrocytes utilizing a polymer-cell construct to produce tissue-engineered cartilage in the shape of a human ear", Plast Reconstr Surg, Aug. 1997;100(2):297-302; discussion 303-4.

Ding, et al., "Chinese Journal of Clinical Rehabilitation", 2006, vol. 10, Issue 5:178-181 pages.

EPO, Communication Pursuant to Article 94(3) EPC for European Patent Application No. 16169070.6, dated Feb. 7, 2019, 5 pages.

Porter, et al., "Biomaterials", 2007, 28:2525-2533 pages.

Porter, et al., "Journal of Biomechanics", 2005, 38:543-549 pages.

Zhao, et al., "Effects of shear stress on 3-D human mesenchymal stem cell construct development in a perfusion bioreactor system: Experiments and hydrodynamic modeling", Biotechnol Bioeng, vol. 96, Issue 3, Feb. 15, 2007, 584-595 Pages.

WIPO, International Search Report mailed for International patent application No. PCT/US14/34559, dated Sep. 23, 2014, 2 pages.

WIPO, IPRP mailed for International Application No. PCT/US2010/026120, Sep. 6, 2011, 6 pages.

WIPO, International Search Report and Written Opinion of the International Searching Authority mailed for International Application No. PCT/US2010/026120, dated Jun. 17, 2010, 8 pages.

Warnke, et al., "Growth and transplantation of a custom vascularised bone graft in a man", Lancet. Aug. 28-Sep. 3, 2004;364(9436):766-70 pages.

EPO, Communication Pursuant to Article 94(3) EPC for European Patent Application No. 16169070.6, dated Aug. 21, 2019, 5 Pages.

* cited by examiner

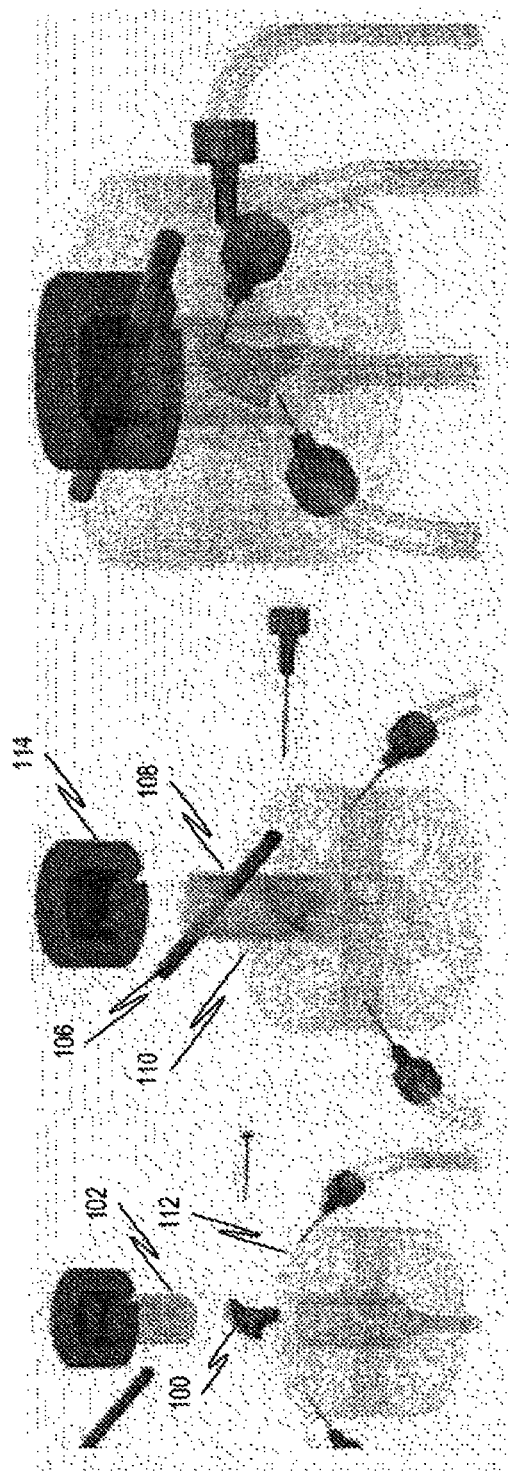

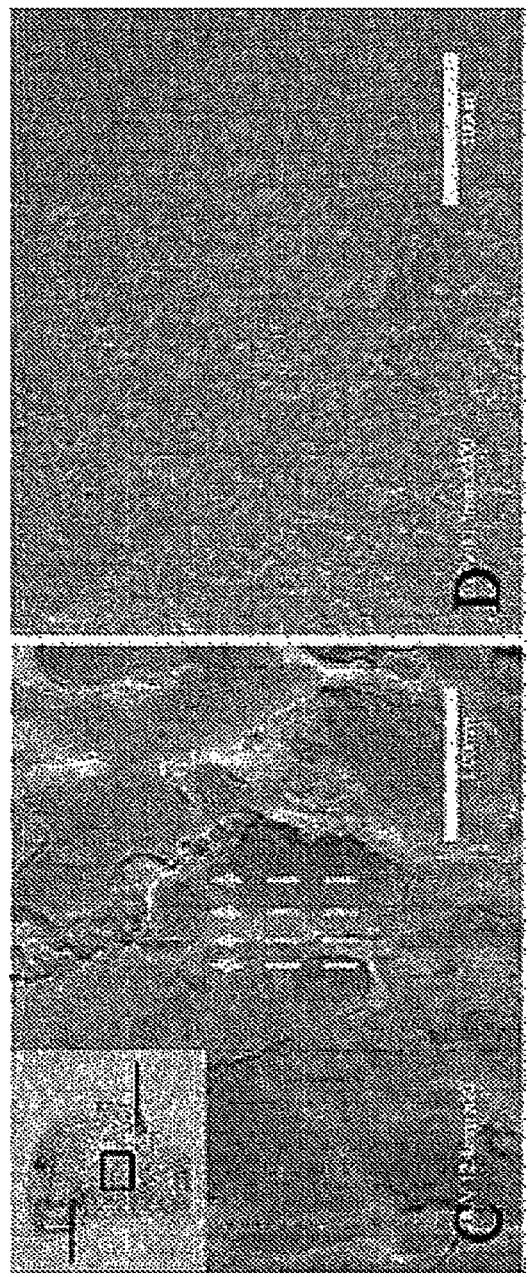

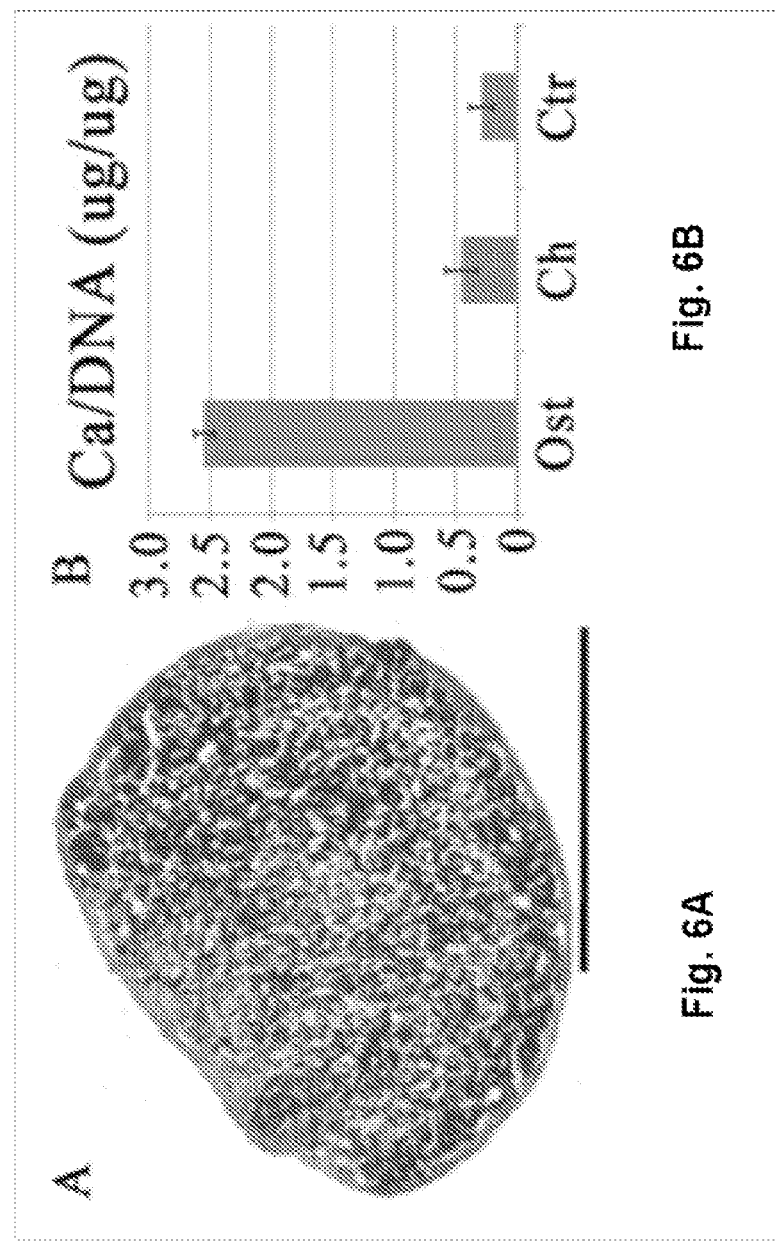

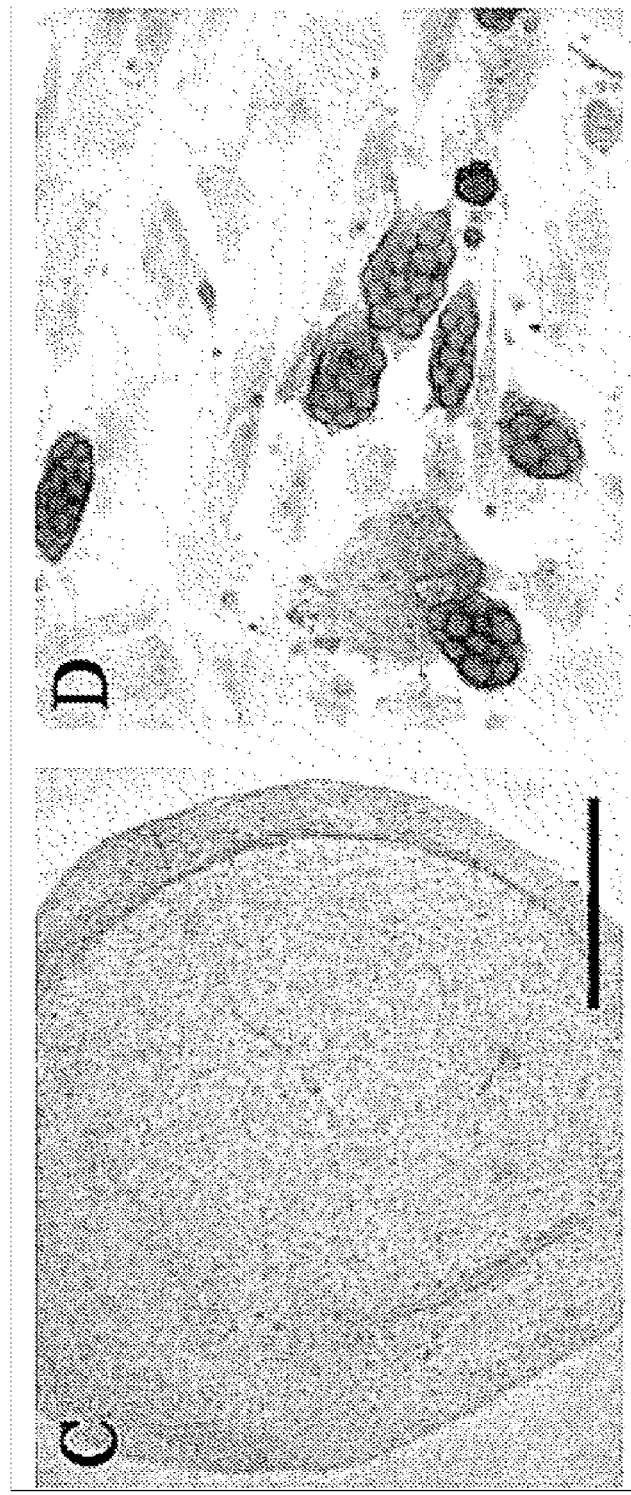

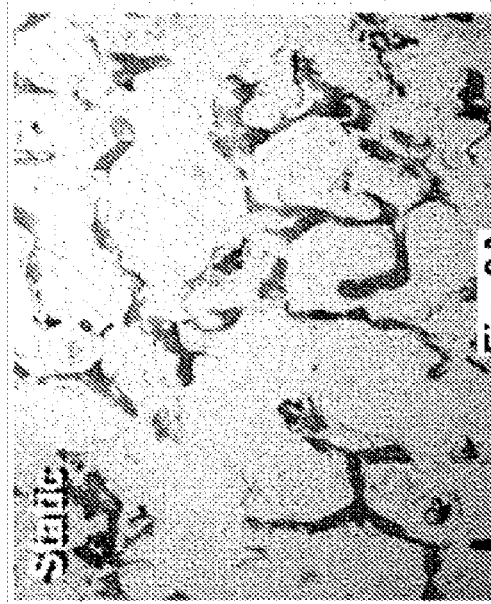
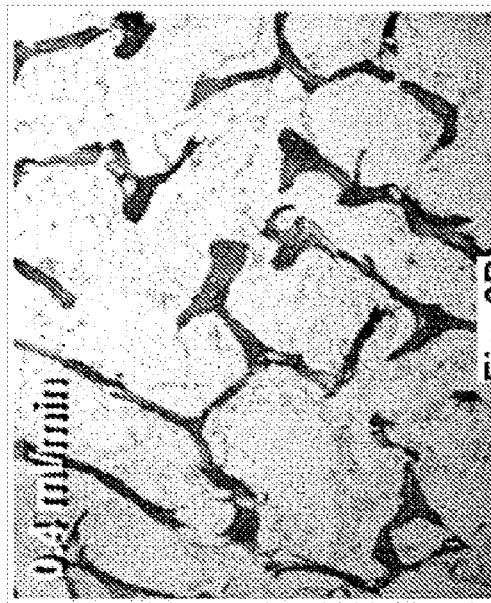
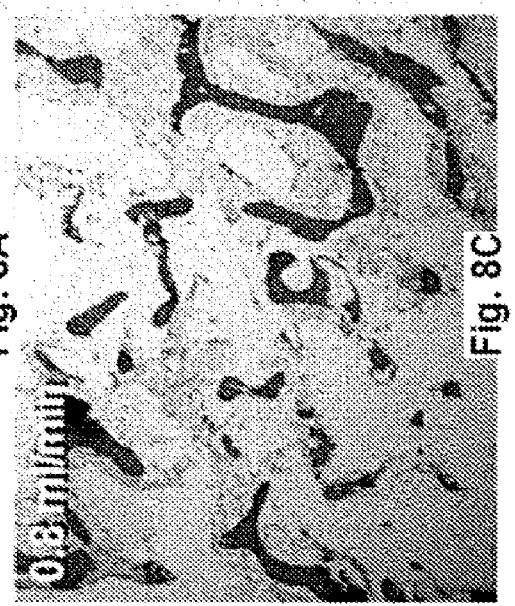

TISSUE ENGINEERING SYSTEM FOR MAKING PERSONALIZED BONE GRAFT

CROSS-REFERENCE TO RELATED APPLICATIONS

This application is a divisional application of U.S. patent application Ser. No. 13/148,735 filed Oct. 28, 2011 which is a National Stage Entry of International Patent Application No. PCT/US10/26120 filed Mar. 3, 2010, which claims the benefit of U.S. Provisional Application No. 61/157,019, filed Mar. 3, 2009, U.S. Provisional Application No. 61/249,999, filed Oct. 9, 2009, and U.S. Provisional Application No. 61/250,166, filed Oct. 9, 2009, all of which are hereby incorporated by reference herein in their entireties.

STATEMENT REGARDING FEDERALLY SPONSORED RESEARCH

This invention was made with U.S. Government support under Grant No. R01 DE161525-01 and P41 EB02520-01A1 awarded by the National Institutes of Health (NIH). The U.S. Government has certain rights in this invention.

FIELD

The present disclosure relates generally to tissue engineering and, more particularly, to methods, devices, and systems for bone tissue engineering.

BACKGROUND

Bone reconstructions often involve autologous tissue grafting. In such a procedure, bone from one part of a patient is used to replace missing or damaged bone in another part of the patient. Because the bone graft is taken from the patient's own body, there is a reduced risk of the patient's body rejecting the graft. However, autologous tissue may be limited due to harvesting difficulties, donor site morbidity, and/or a clinician's ability to contour delicate three dimensional shapes.

SUMMARY

The availability of personalized bone grafts engineered from the patient's own stem cells may revolutionize the way bone defects are currently treated. A 'biomimetic' approach utilizes stem cells, regulatory factors, and appropriate scaffolds to guide cell differentiation and assembly into the desirable tissue phenotypes. Thus, an anatomically-shaped, human bone graft may be cultivated ex vivo using a bioreactor capable of perfusing large complex porous scaffolds. Scaffolds derived from image-based modeling of a target can be seeded with human mesenchymal stem cells (hMSCs) and cultivated. The bioreactor encloses the scaffold and controls flow for perfusion of the cells. Dense uniform cellular growth can be attained throughout the entire construct as a result of the medium perfusion. In embodiments, the bioreactor has a mold into which perfusion medium is pumped under pressure and ports at multiple sites through which the medium can enter and/or exit the mold.

In embodiments, a method of making a bone graft can include shaping a scaffold according to a target shape of bone to be replaced, forming a support with a cavity which closely conforms to the scaffold resulting from the shaping, and pumping a perfusate into the cavity while simultaneously receiving perfused perfusate through outlets sealed at multiple points to and about the scaffold. The multiple points can be separated and arranged such that the perfusate enters the scaffold over a substantial surface thereof and exits the scaffold at the multiple points.

In embodiments, a bone graft can include a scaffold having cells. The cells can be arranged such that they have a density pattern that is responsive to a flow pattern of perfusate through the scaffold. The flow pattern can include a gradient of decreasing cell density stemming from focuses at a surface of the scaffold.

In embodiments, a method of making a tissue structure can include forming an image of a target tissue structure, shaping a three-dimensional scaffold responsively to the image, and seeding the scaffold with cells. The method can also include delivering nutrients to the cells within and on the surface of the scaffold by flowing a nutrient fluid into a tightly conforming vessel holding the scaffold, through multiple first surface portions of the scaffold, and out through at least one second surface portion.

In embodiments, a tissue engineering system can include a machining device, a bioreactor, and a flow mechanism. The machining device can be configured to machine a three-dimensional vessel with an internal surface closely following a shape of a target anatomy of a patient. The bioreactor can have a recess configured to receive said vessel and outlet ports configured to accept at least one lumen and to permit flow communication between the at least one lumen and an internal volume defined by the internal surface of said vessel. The flow mechanism can be configured to remove a perfusate from the at least one lumen and return it to the internal volume of the vessel.

In embodiments, a method for making a bone tissue structure can include seeding a porous scaffold with mesenchymal stem cells, and perfusing culture medium throughout an interstitial volume of the porous scaffold for a period of time such that the mesenchymal stem cells develop lamellae of bone tissue which fills pore spaces of the scaffold.

BRIEF DESCRIPTION OF DRAWINGS

FIGS. 1G-1H and 1J show various steps in the assembly of a bioreactor, according to one or more embodiments of the disclosed subject matter.

FIGS. 5C through 5F are images showing characteristics of cultivated tissue grafts, according to one or more embodiments of the disclosed subject matter.

FIG. 6A is an image showing a von Kossa stain of histological sections of pellets cultured under osteogenic conditions, according to one or more embodiments of the disclosed subject matter.

FIG. 6B is a chart showing calcium content normalized to DNA values of cell pellets cultured for four weeks in osteogenic (ost), chondrogenic (ch), or control (ctr) media.

FIG. 6C is an image showing alcian blue stains of cell pellets cultured under chondrogenic conditions.

FIG. 6D is an image showing oil Red 0 stains of lipid droplets in pellets cultured under adipogenic conditions.

FIGS. 8A through 8D are images showing the effects of perfusion flow rate on cell density, according to one or more embodiments of the disclosed subject matter.

DETAILED DESCRIPTION

Figure 1B:
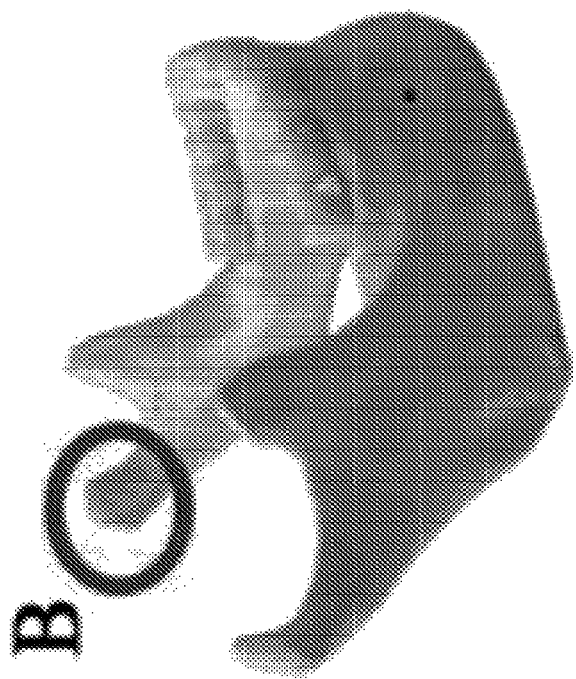
FIGS. 1A-1B are an images of a human jawbone showing a location of a TMJ condyle with respect thereto.

The availability of personalized bone grafts engineered from a patient's own stem cells has the potential to alter the way bone defects are currently treated. Bone grafts with a high degree of shape fidelity can be produced, which have a low risk of rejection by the patient's body. The functionality of engineered bone grafts can be evaluated by the mechanical properties and the ability of cells to make tissue specific proteins. Craniofacial bone grafts also have the characteristic that their functionality is linked to their overall geometry.

Bone grafts of high utility for reconstructive surgery can be based on "designer scaffolds" shaped into gross geometries specific to the patient and the defect being treated. Anatomically shaped, viable human bone grafts can be engineered using human mesenchymal stem cells (hMSCs) and a "biomimetic" scaffold bioreactor system. The disclosed techniques may be used to engineer tissue structures such as bone grafts, including but not limited to autografts. The hMSCs may be suited for use in cranial and maxillofacial applications due to their easy accessibility, capability for in vitro proliferation, and the potential to form cartilage, bone, adipose and vascular tissues.

The potential of hMSCs for differentiation potential along mesenchymal lineages may be characterized for each batch of cells by culturing cell pellets under osteogenic, chondrogenic, and adipogenic conditions for a culture period of time, for example, four weeks. FIG. 6A shows a von Kossa stain of histological section of hMSC pellets cultured under osteogenic conditions. FIG. 6B is a graph illustrating the calcium content of hMSC pellets cultured for four weeks in osteogenic (ost), chondrogenic (ch), or control (ctr) medium. The data in FIG. 6B has been normalized with respect to DNA values. FIG. 6C represents an alcian blue stain of hMSC pellets cultured under chondrogenic conditions, while FIG. 6D is an image of an oil red O stain of liquid droplets of hMSC cell pellets cultured under adipogenic conditions. Thus, hMSCs have been pre-differentiated along chondrogenic and osteogenic lineages. Moreover, the hMSCs can form distinct osseous and cartilaginous regions. However, other types of stem cells may also be used according to one or more contemplated embodiments.

In vitro control of cell viability and tissue development in clinically sized and shaped bone tissue constructs determines their utility for regenerative medicine. The enhancement of mass transport and the generation of hydrodynamic shear, which are important for bone development and function, may require interstitial flow. Thus, described herein are tissue engineering devices, systems, and methods for creating in vitro an entire bone condyle containing viable cells at physiologic density and well-developed bone matrix. In embodiments, hMSCs can be induced to form bone on a de-cellularized scaffold that has the exact geometry of the desired bone structure. For example, the desired bone structure may be a temporomandibular joint (TMJ) condylar bone, as circled in FIGS. 1A-1B.

The hMSCs can be induced to form bone on the scaffold using an "anatomical" bioreactor with control of interstitial flow. Flow patterns associated with the complex geometry of the bone graft provide a unique opportunity to correlate the architecture of the forming bone with interstitial flow characteristics, under controllable in vitro conditions. This approach can help provide a variety of anatomically shaped bone grafts designed to meet the needs of a specific patient and a specific craniofacial or orthopedic reconstruction. Other applications will also be evident from the present disclosure.

In embodiments, anatomically-shaped scaffolds may be generated by CNC machining fully de-cellularized (e.g., trabecular) bone based on digitized images of the desired bone structure. For example, the trabecular bone may be derived from the subchondral region of the knee joint of a calf and subsequently treated to remove any cellular material. The bone may be washed with high velocity water to remove marrow and then subject to a wash for 1 hour in PBS with 0.1% EDTA (w/v) at room temperature. The bone may then be subject to sequential washes in hypotonic buffer (10 mM Tris, 0.1% EDTA (w/v)) overnight at 4° C., detergent (10 mM Tris, 0.5% SDS (w/v)) for 24 hours at room temperature, and enzymatic solution (50 U/mL DNAse, 1 U/mL RNAse, 10 mM Tris) for 3-6 hours at 37° C. to remove any remaining cellular material. Alternatively, other types of scaffold material may be used. For example, the scaffold may be formed from other naturally occurring material such as coral, a synthetic material such as a ceramic or polymer, and/or other natural or synthetic porous structures.

In embodiments, the de-cellularized trabecular bone can be seeded with hMSCs and cultured with interstitial flow of culture medium. A bioreactor with an internal chamber in the exact shape of the desired human bone (e.g., a human TMJ) controls perfusion throughout the engineered scaffold. After a cultivation period (e.g., 5 weeks), tissue growth can be evidenced by the formation of confluent layers of lamellar bone (by scanning electron microscopy), markedly increased volume of mineralized matrix (by quantitative microcomputer tomography), and the formation of osteoids (histologically). Experiments have shown that cells in such a construct are fully viable at a physiologic density, which is a desirable property in grafts. Moreover, the density and architecture of bone matrix correlated with the intensity and pattern of the interstitial flow, as determined in experimental and modeling studies.

Figure 1A:
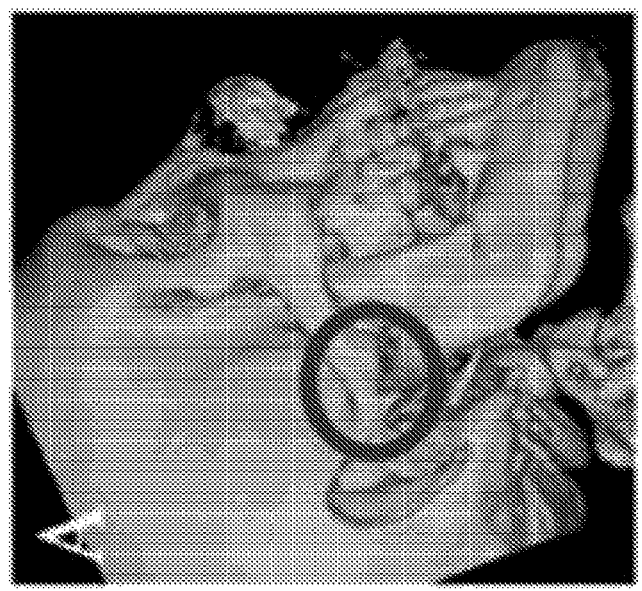
Figure 1C:
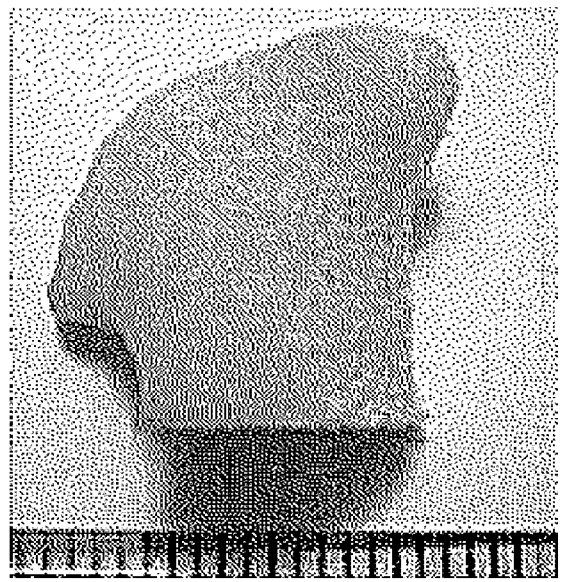
FIG. 1C is an image of a de-cellularized scaffold, according to one or more embodiments of the disclosed subject matter.

In an embodiment, the anatomical shape of a bone structure, for example the TMJ of a patient, can be defined from digitized medical images, such as the circled portions in FIGS. 1A-1B. The TMJ has clinical importance and a complex shape, which may be desirable for evaluating and demonstrating the tissue engineering techniques and devices described herein. However, the techniques and devices described herein are equally applicable to other types of bones and shapes as well. The shape of the bone structure can be faithfully reproduced by machining a de-cellularized trabecular bone scaffold. For example, the scaffold can be prepared by milling the de-cellularized bone based on clinical computerized tomography (CT) images of the patient representing the exact geometry of the human TMJ condyle. An example of such a milled scaffold for a TMJ condyle is shown in FIG. 1C. The CT image data can be fed to an appropriate computer-assisted machining device in order to form an appropriately shaped scaffold from fully de-cellularized trabecular bone. Although the shape of a TMJ condyle has been shown and discussed for the scaffold, other shapes are of course possible depending on the desired bone graft.

The hMSCs may be cultured up to the $3^{rd}$ passage and then used for seeding the scaffolds. After, seeding, the scaffolds may be cultured with osteogenic medium, such as Dulbecco's Minimal Essential Medium (DMEM) supplemented with 10% fetal bovine serum (FBS), 1% penicillin-streptomycin, 100 nM dexamethasone, 10 mM beta-glycerophosphate, and 50 mM ascorbic acid-2-phosphate. The machined scaffold can be seeded in a stirred suspension of hMSCs, for example, at a density of $10^6$ cells/ml. The scaffold may then be precultured statically for an additional period of time, for example, 1 week, to allow for cell attachment. The cell-seeded scaffolds may then be transferred into the "anatomical" bioreactor chambers and hydrodynamic shear applied by starting the medium perfusion. Perfusion using the bioreactor can then be performed for an additional period of time, for example, 4 weeks.

Figure 1D:
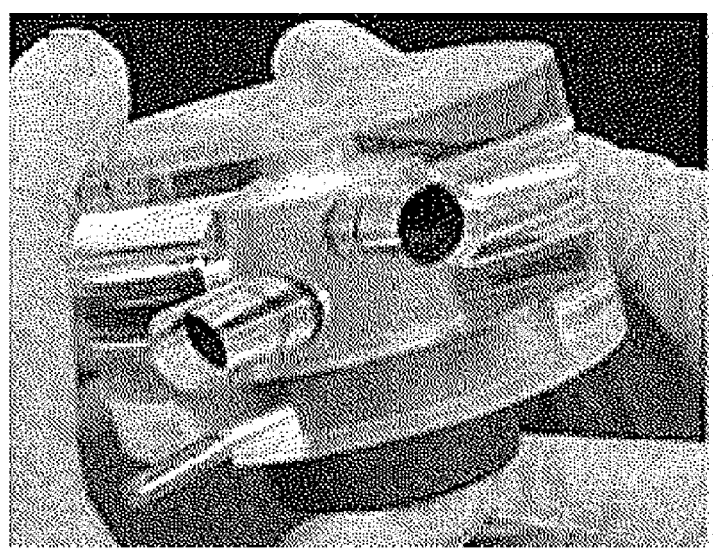
FIG. 1D is an image of an assembled bioreactor, according to one or more embodiments of the disclosed subject matter.
Figure 1E:
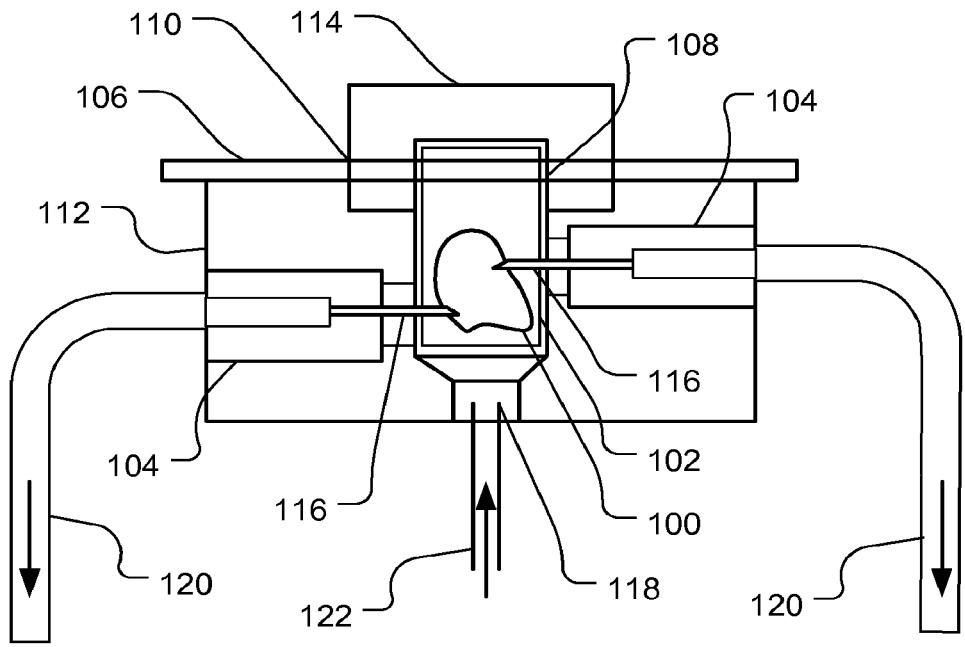
FIG. 1E is a schematic diagram showing a bioreactor with a scaffold contained therein, according to one or more embodiments of the disclosed subject matter.
Figure 1F:
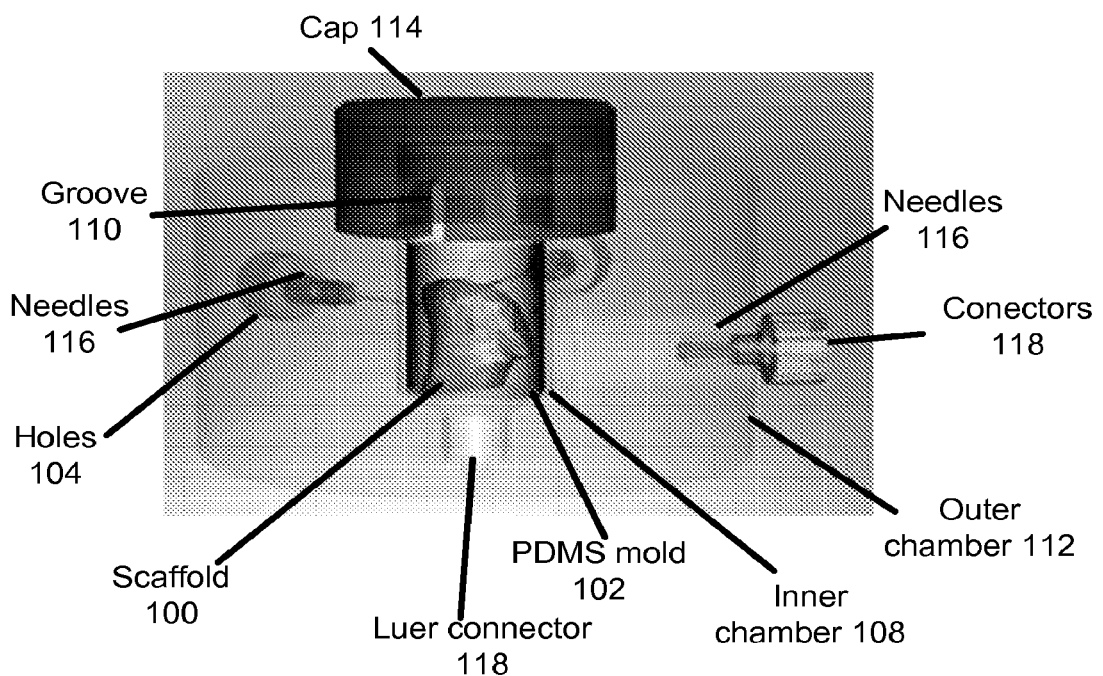
FIG. 1F is a side view of a three-dimensional model of a bioreactor with a scaffold contained therein, according to one or more embodiments of the disclosed subject matter.

FIGS. 1D-1F illustrate a perfusion bioreactor system according to an embodiment of the present disclosure. The perfusion bioreactor system is designed to control the perfusion path through a geometrically complex scaffold 100. An anatomically shaped mold 102 holds the scaffold 100. Because of its modular design, the bioreactor chambers can accommodate different geometries by simply inserting a different mold 102 of appropriate shape, created, for example, by using digitized medical images. In addition, the bioreactor can be made from materials which allow for noninvasive visualization and monitoring of medium distribution within the tissue scaffolds throughout the cultivation period The interior of the bioreactor is designed to conform to the surface of the scaffold. For example, the interior of the bioreactor can be formed using a polydimethylsiloxane (PDMS) mold. The PDMS mold can be created by pouring PDMS around a CNC-milled piece of delrin (acetal copolymer) generated from the digital images so as to exactly duplicate the shape of the bone scaffold 100. Once the PDMS has cured, the delrin is removed. The scaffold 100 can then be placed into the PDMS mold 102 and inserted into the bioreactor. The PDMS mold 102 thus forms an inner cavity within inner chamber 108 for holding the scaffold 100 therein. Although molding of PDMS has been described, other materials and techniques may also be employed to produce the closely-conforming inner cavity housing the scaffold within the bioreactor.

A system providing software for generating machine instructions for fabricating the scaffold and/or the holding fixture (in examples, corresponding to mold 102) may also be provided. The software may take images of the target anatomy and produce instructions for machining the holding fixture or vessel to have close conforming walls as described with respect to mold 102 above. The system could also be provided with a milling device for making a positive structure to create the mold or a negative structure for the mold itself.

Other types of "machining" are also possible, such as, but not limited to, 3-D printing or rapid prototyping/fabrication systems (e.g., computer guided photopolymerizing device).

FIGS. 1G-1H and 1J show steps in the assembly of the exemplary bioreactor. A bone scaffold 100 is assembled with the mold 102 and placed into the inner chamber casing 108 of the bioreactor. The inner chamber casing 108 may be made of, for example, polypropylene or polystyrene. A metal rod 106 is placed through preformed holes in the mold 102 and inner chamber casing 108 so as to align the assembly with groove 110 in outer chamber 112. Outer chamber 112 may be made of, for example, clear acrylic. For example, the outer chamber of the bioreactor can have an external diameter of 7.5 cm and a height of 5 cm. However, other suitable materials and sizes may also be used for the bioreactor according to one or more contemplated embodiments. By virtue of the alignment provided by rod 106, the assembly and the scaffold therein can be maintained in the correct orientation, as shown in FIG. 1H. The assembly of the scaffold 100, mold 102, and inner chamber casing 108 is inserted into the outer chamber 112, which is then tightly capped with a top 114. The top 114 may be made of, for example, polyetherimide (PEI). Top 114 may also have a groove therein so as to accommodate rod 106 when sealing the inner chamber 108 and outer chamber 112.

The outer chamber 112 and cap 114 also serve to compress mold 102 around the scaffold 100, thereby forcing culture medium to flow through the entire scaffold rather than channeling around the periphery thereof. The outer chamber 112 can have a plurality of radial cylindrical ports, for example, holes 104. For example, the outer chamber 112 can have six ports arranged equidistant around the circumference of the outer chamber (i.e., at 60° intervals). Each of the cylindrical ports can serve as a guide for controlling the exact position and depth for the insertion of a needle 116 into scaffold 100, the purpose of which is discussed in greater detail below. For example, needle 116 may be a 23 gauge needle. Snugly fitting delrin rings may be placed into each hole 104. The center of the delrin rings may be tapped so as to accommodate nylon screws which have been cored to fit the 23 gauge needles therein. The needles may be place into the nylon screws such that the ends of the needles protrude from the screws. When screwed into the delrin rings, the nylon screw assembly allows the needle to penetrate into the scaffold in the inner chamber to serve as an inlet/outlet port for medium flow.

In an alternative, one or more outlet ports of may be provided in and around the scaffold to evenly distribute fluid through the scaffold and allow full perfusion of the interstitial areas of the scaffold. Such outlet ports may be smaller than the inlet port. In still another alternative, one or more of the needle ports 116 can serve as an inlet while connector 118 simultaneously serves as an outlet for perfusing the scaffold. In yet another alternative, one or more of the needle ports 116 can serve as an inlet while connector 118 simultaneously serves as an inlet for perfusing the scaffold.

The location of each hole 104 may be determined, for example, using computer-aided design based on a three-dimensional reconstruction of the desired bone structure. In embodiments, three of the six ports 104 can be used as outlets. An additional port, aligned with the central axis of the inner chamber 108, can be connected to tubing 122 via a connector 118 (e.g., a luer connector). This central port can serve as a single inlet for medium to enter scaffold 100. Thus, flow can enter via tubing 122 into the inner chamber 108, perfuse through scaffold 100, and exit through three (or more) needle outlets 116. Tubing 120 connected to the needle outlets 116 can convey the perfused fluid therefrom. In an alternative, the flow of medium may be reversed such that culture medium enters the mold 102 through needles 116, perfuses through scaffold 100, and exits via tubing 122.

The flow rate of medium exiting through outlet ports 104 via tubing 120 can be regulated such that the flow rate for each outlet is equal. Such regulation may be accomplished, for example, by adjusting clamps on tubing 120. Alternatively, inline flow regulators or valves may be used to control the flow rate of each outlet. Of course, other flow regulation mechanisms are also possible according to one or more contemplated embodiments. Moreover, the flow rate for each outlet need not be equal. Rather, the flow rate may be controlled to achieve a desired flow profile conducive to cell growth as determined from computer-aided flow modeling and/or experimentation.

Figure 1K:
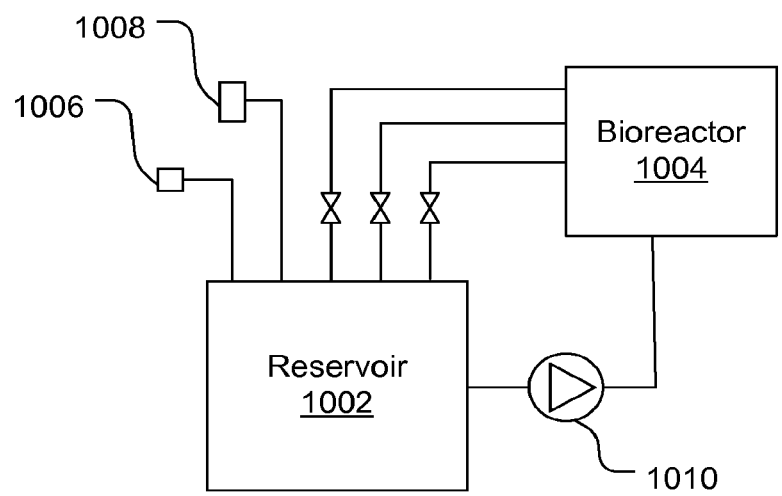
FIG. 1K is a schematic diagram of an apparatus for perfusion support for a bioreactor, according to one or more embodiments of the disclosed subject matter.

As shown in FIG. 1K, culture medium perfused through the bioreactor 1004 can be conveyed via pump 1010 back into a reservoir 1002 for reuse. The reservoir 1002 may also serve as a bubble trap with an air outlet 1008. The pump 1010, which may be, for example, a low-flow multi-channel digital peristaltic pump, can recirculate the culture medium from the reservoir 1002 into the bioreactor. The medium in the reservoir 1002 may be changed periodically through port 1006 of the reservoir. For example, a syringe can be attached to port 1006 to sterilely remove culture medium from and add culture medium to the reservoir without disturbing the operation of the bioreactor 1004. The reservoir may contain an initial volume of, for example, 40 ml of culture medium. Half of the culture medium in the reservoir may be replaced, for example, every three days.

Tissue engineering of large bone constructs requires flow through the interstices and/or pores of the scaffold for efficient transport of nutrients and waste materials between the cells and culture medium. In addition, interstitial flow allows for direct exposure of cells to hydrodynamic shear, which may be important for osteogenesis. The volumetric flow-rate (e.g., 1.8 ml/min) and the corresponding superficial velocity (e.g., an average of 0.06 cm/s) can be selected to sustain dense tissue growth throughout the scaffold. For example, the flow-rates may be selected so as to be within the range of flow-rates and superficial velocities that stimulate osteogenic differentiation of hMSCs.

The cells can be cultured in a scaffold that has the structural, biochemical and mechanical properties of native bone and the actual geometry of the final graft. For example, the scaffold can be formed from fully de-cellularized bone, which has been machined, for example, by image-guided fabrication, to achieve the desired geometry of the final graft. The void volume of such a de-cellularized bone was determined by micro-CT analysis to be greater than 80%. SEM and histological analysis of de-cellularized bone also revealed pore sizes of approximately 1 mm. Such structural features may enable efficient and spatially uniform dynamic seeding of hMSCs into the scaffolds. Histological evaluation of freshly seeded scaffolds demonstrated that hMSCs lined the internal pore walls, while leaving pore spaces unobstructed.

Figures 7A, 7B, 7C:
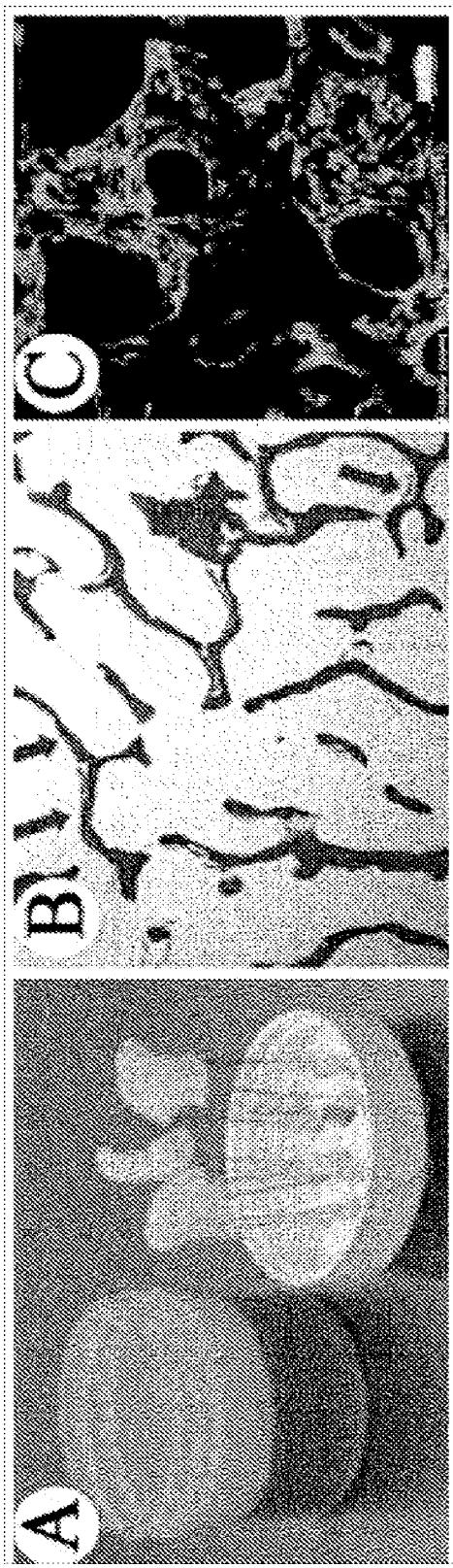
FIG. 7A is an image of a spinner-flask apparatus used to seed cells into scaffolds, according to one or more embodiments of the disclosed subject matter.
FIG. 7B is an image showing H & E stains of scaffolds one day after seeding.
FIG. 7C is an image showing live-dead stains of scaffolds one day after seeding.

Referring now to FIG. 7A, a spinner flask (cap shown with TMJ constructs) can be used to seed cells into TMJ scaffolds. FIG. 7B show a hemotoxylin and eosin (H&E) stain of a scaffold one day after seeding. As is evident from FIG. 7B, pore spaces in the scaffold remain open, and cells can be found only along the walls of the pores (see arrows in FIG. 7B). FIG. 7C shows a live-dead stain of a scaffold one day after seeding. As is evident from FIG. 7C, a high percentage of viable cells can be retained throughout the seeding process.

After one hour, the seeding efficiency was found to be $34.0 \pm 7.1\%$, resulting in approximately $3.4 \times 10^6$ cells per construct attaching in a spatially uniform manner Scaffolds were cultured statically for one week prior to placing in the bioreactors, enabling firm cell attachment and deposition of extracellular matrix before the exposure to hydrodynamic shear forces. Of course, other methods and devices for seeding of the scaffolds are contemplated.

After seeding, the scaffold may be assembled under sterile conditions into the bioreactor, as discussed with respect to FIGS. 1G-1H and 1J. Quick assembly can maintain cell viability in the scaffold throughout the process. Using the bioreactor, culture medium can be perfused throughout the entire scaffold. For a given flow rate, equal outlet flow rates are maintained at each of the three outlets, although differential outlet flow rates are also possible. The optimal inlet flow rate could be determined based on fluid flow analysis, computer-aided modeling, or experimental data. For example, the inlet flow rate may be between 0.4 ml/min and 1.8 ml/min. Experimental evaluation of cell density and distribution after 5 weeks of culture suggests that 1.8 ml/min may yield the best cell distribution and most rapid tissue development for the disclosed bioreactor. Based on micro-CT analysis, the average cross-sectional area through the scaffolds in the direction of flow was determined to be 0.5 $cm^2$.

For this cross-sectional area, the 1.8 ml/min inlet flow rate corresponds to an average superficial flow velocity of 0.06 cm/s. However, other flow rates and/or superficial flow velocities may be chosen depending on, for example, bioreactor geometry, stem cell type, scaffold size, scaffold type, and/or pore size.

Due to the complex distribution of flow within the tissue scaffolds, flow rates as high as 0.15 cm/s are possible in certain scaffold regions, and as low as 0.0001 cm/s in other scaffold regions. In the whole range of these flow velocities, hMSCs may maintain complete viability and exhibit characteristics of osteogenic differentiation. There is also no apparent threshold in fluid flow rate after which perfusion becomes detrimental to hMSCs. It is therefore possible that tissue growth can be further improved by increasing the flow rates in the bioreactor above the 1.8 ml/min inlet flow rate described above.

Final cell densities were approximately $105\text{-}210 \times 10^6$ cells/ml. Such high cell densities may be important for functional bone tissue formation for cell-cell interaction. For statically cultured constructs, the loose packing of cells (indicated by SEM) and only minimal osteoid formation (indicated by histology) provided evidence of limited functional differentiation of the hMSCs in the inner regions of these constructs. For bioreactor cultured constructs, various imaging modalities, discussed in detail below, confirmed that cells formed dense tissues throughout the construct volumes, leading to larger increases in bone volume.

Referring to FIGS. 8A through 8D, the effects of perfusion flow rate on cell density in a scaffold are shown. FIGS. 8A-8D are H&E stains of the central regions of scaffolds cultivated for 5 weeks under various flow conditions. FIG. 8A was cultivated under a static (i.e., no flow) condition. FIG. 8B was cultivated under a 0.4 ml/min inlet flow rate. FIG. 8C was cultivated under a 0.8 ml/min inlet flow rate. FIG. 8D was cultivated under a 1.8 ml/min inlet flow rate. As is evident from FIGS. 8A-8D, increasing the flow rate led to increasingly dense matrix deposition in the pore spaces.

Figures 2, 3A:
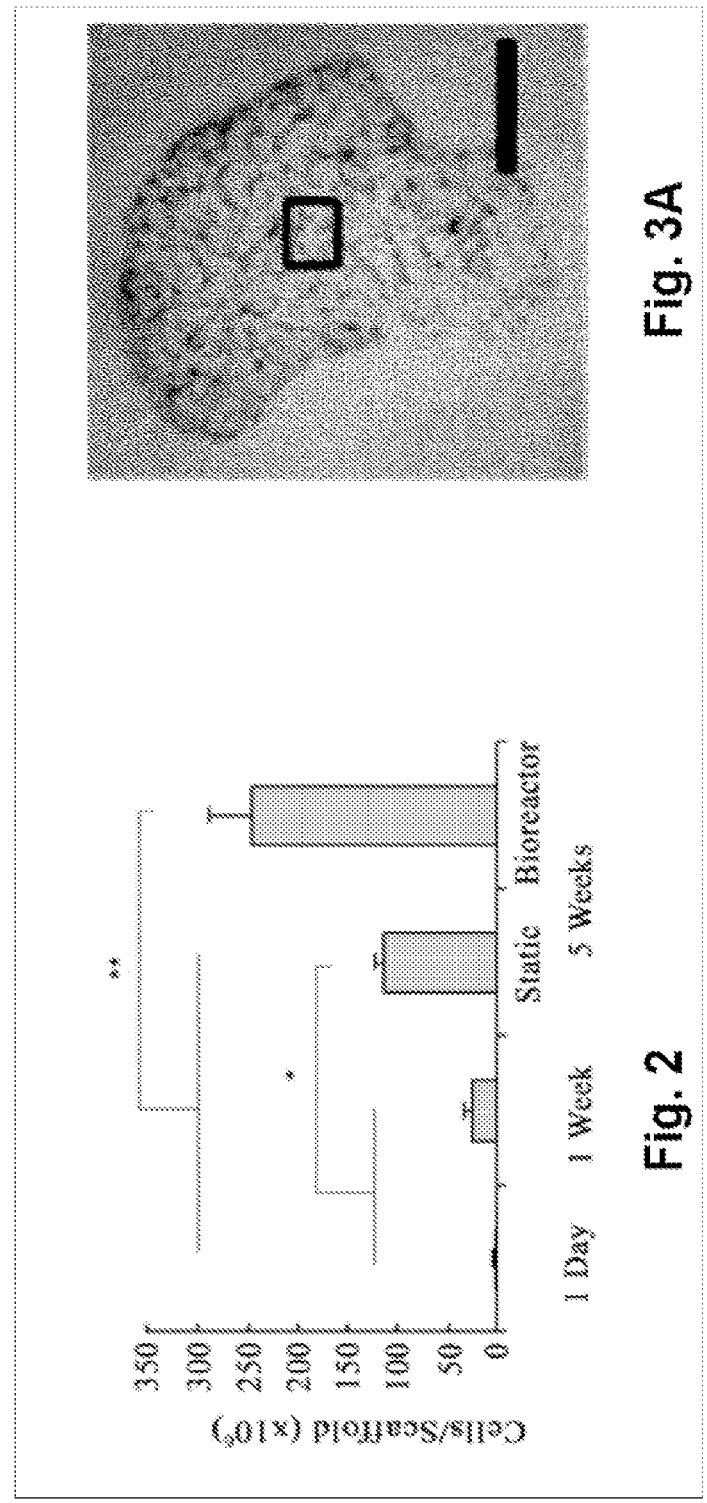
FIG. 2 is a chart showing cultivated cell count under various conditions, according to one or more embodiments of the disclosed subject matter.
FIGS. 3A through 3H are images of exemplary bone constructs formed under various conditions, according to one or more embodiments of the disclosed subject matter.

By perfusing the scaffold in the disclosed manner using the bioreactor, cells are able to proliferate in the scaffold so as to form a viable bone graft. In experiments, cells proliferated extensively over the first week of culture, as evidenced by an approximately 7.5-fold increase in DNA content. The DNA content continued to increase throughout the cultivation period under both static (4.5 fold increase) and perfused (10 fold increase) culture conditions resulting in overall 37 and 75 fold increases, respectively, in cell numbers relative to initial seeding values. Referring now to FIG. 2, cell numbers increased with time of culture and medium perfusion. From day 1 to day 7, the cell numbers increased 7.5-fold, from $3.4 \times 10^6$ to $25 \times 10^6$ cells/scaffold. Over the subsequent 4 weeks, cell numbers in static culture increased 4.5-fold, to approximately $110 \times 10^6$ cells/scaffold, whereas the increase in perfused bioreactor culture was 10-fold, to approximately $250 \times 10^6$ cells/scaffold.

Figure 3C:
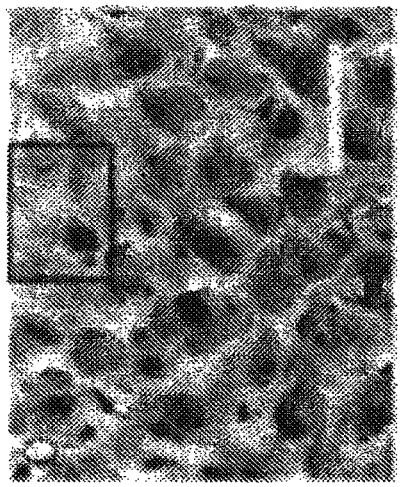
Figure 3E:
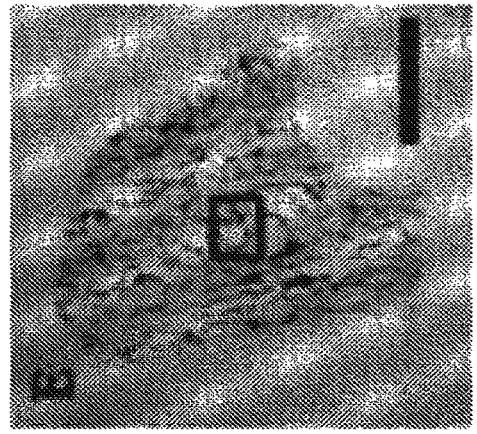
Figure 3B:
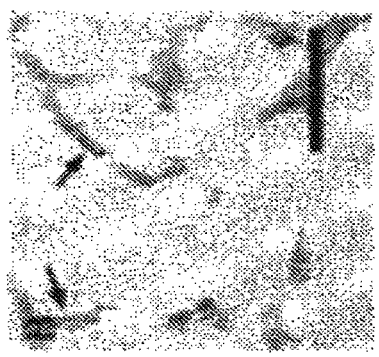
Figure 3D:
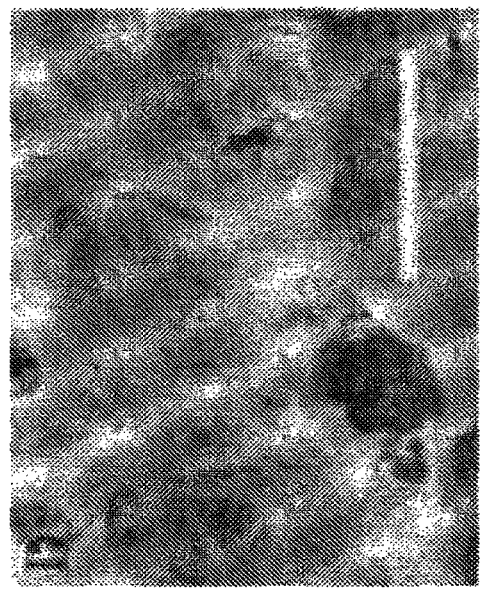
Figure 3F:
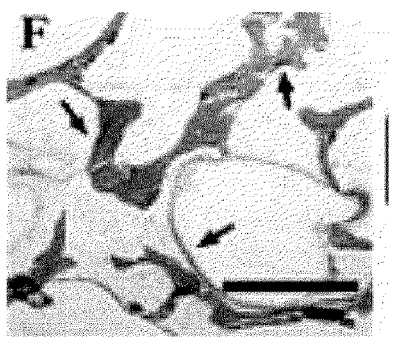

Referring now to FIGS. 3A through 3H, bone formation was also markedly enhanced by perfusion in a manner responsive to the fluid flow pattern. FIGS. 3A-3D show scaffolds cultured under static conditions while FIGS. 3E-3H show scaffolds cultured with medium perfusion in the disclosed bioreactor. FIGS. 3A and 3E show trichrome staining of entire cross-sections of scaffolds, which illustrate differences in the new matrix distribution compared to the original scaffold for the static (FIG. 3A) and perfused (FIG. 3E) culture groups. Moreover, significant differences can be observed in osteoid formation (arrows) in the central regions of scaffolds cultured statically (FIG. 3B) and in perfusion (FIG. 3F).

Figure 3G:
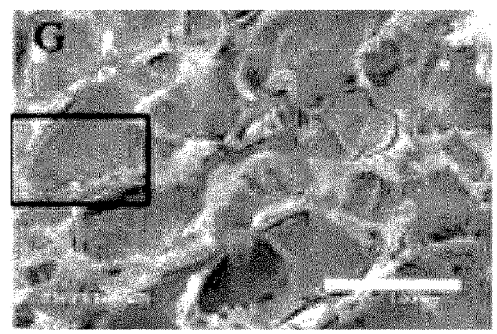
Figure 3H:

FIGS. 3C, 3D, 3G, and 3H are SEM images of the central scaffold regions. In particular, FIGS. 3C and 3D show that statically cultured scaffolds exhibit empty pore spaces and loosely packed cells. In contrast, FIGS. 3G and 3H show that scaffolds cultured in perfusion demonstrate formation of dense and confluent lamellae of bone tissue that filled the entire pore spaces. Measured increases in cell numbers with time and culture regimen have been corroborated with imaging data. Scaffolds cultivated under static conditions formed new matrix primarily at the periphery (FIG. 3A), whereas bioreactor-grown scaffolds displayed new tissue growth throughout their volumes (FIG. 3E). Histological sections demonstrated stark contrast in cell growth and osteoid formation patterns in the central regions between the two culture groups (FIGS. 3B and 3F). The new osteoid area normalized to existing bone trabeculae in the central regions of static scaffolds was $0.031 \pm 0.013$ mm$^2$/mm$^2$ as compared to $0.210 \pm 0.022$ mm$^2$/mm$^2$ for perfused scaffolds (i.e., a 7-fold increase due to perfusion). SEM images of the inner regions of the tissue scaffolds corroborated these findings yet were uniquely instructive. The inner regions of static scaffolds showed pore spaces that were empty or only loosely packed with the cells and matrix (FIGS. 3C and 3D), in contrast to perfused scaffolds, which showed densely packed pore spaces throughout their entire volumes (FIGS. 3G and 3H).

Figure 4A:
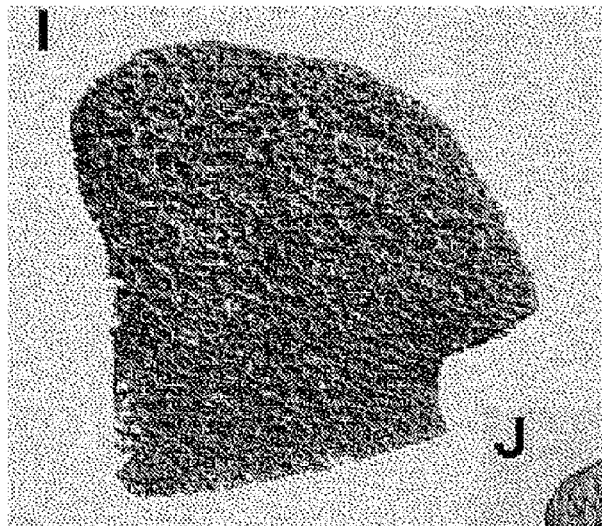
FIGS. 4A through 4C are images of a bone scaffold illustrating changes in the scaffold due to perfusion over time, according to one or more embodiments of the disclosed subject matter.
Figure 4B:
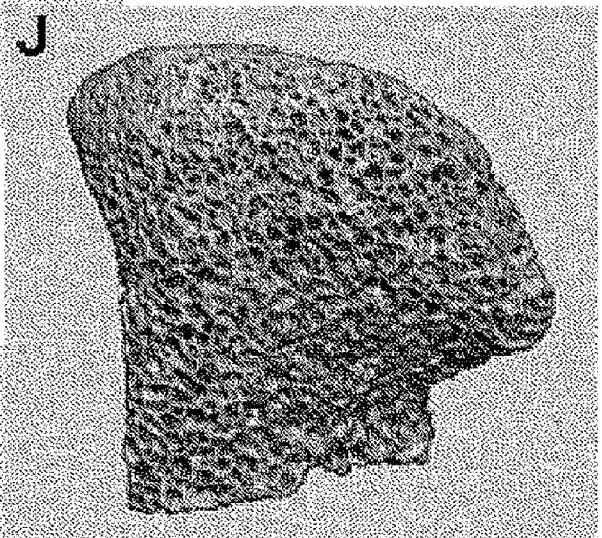
Figure 4C:
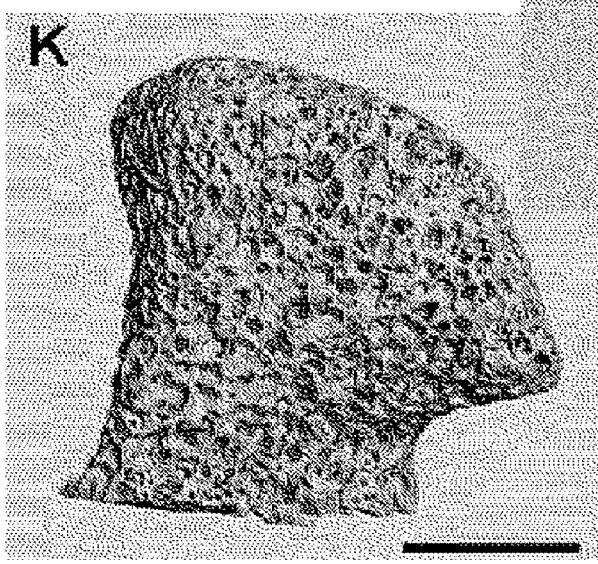

FIGS. 4A through 4C are reconstructed images of a bone scaffold taken by a three-dimensional micro-CT illustrating changes in the scaffold for various perfusion times. FIG. 4A was taken at a time at the beginning of the perfusion process, FIG. 4B in the middle of the perfusion process, and FIG. 4C near the end of the perfusion process. In particular, these figures illustrate the development of the architecture of the mineralized bone matrix of the scaffold over time and in a manner dependent on culture conditions. The images thus demonstrate the changes in pore structure (relative to the initial state) that were evident at the end of the 5-week cultivation period. Bioreactor scaffolds exhibited more rapid deposition of new mineral matrix as compared to static scaffolds. The mineral deposition in pore spaces is also evident from FIGS. 4A-4C. Statistically significant increases in bone volume were observed with time of culture in both static (8.7%) and perfused (11.1%) scaffolds, with consequent increases in trabeculae number (Tb. N*) and thickness (Tb. Th), and decreases in trabecular spacing (Tb. Sp*). The structural model index (SMI) numbers for static and perfused scaffolds were lower after cultivation indicating a trend toward the formation of plate-like trabeculae.

Figures 5A, 5B:
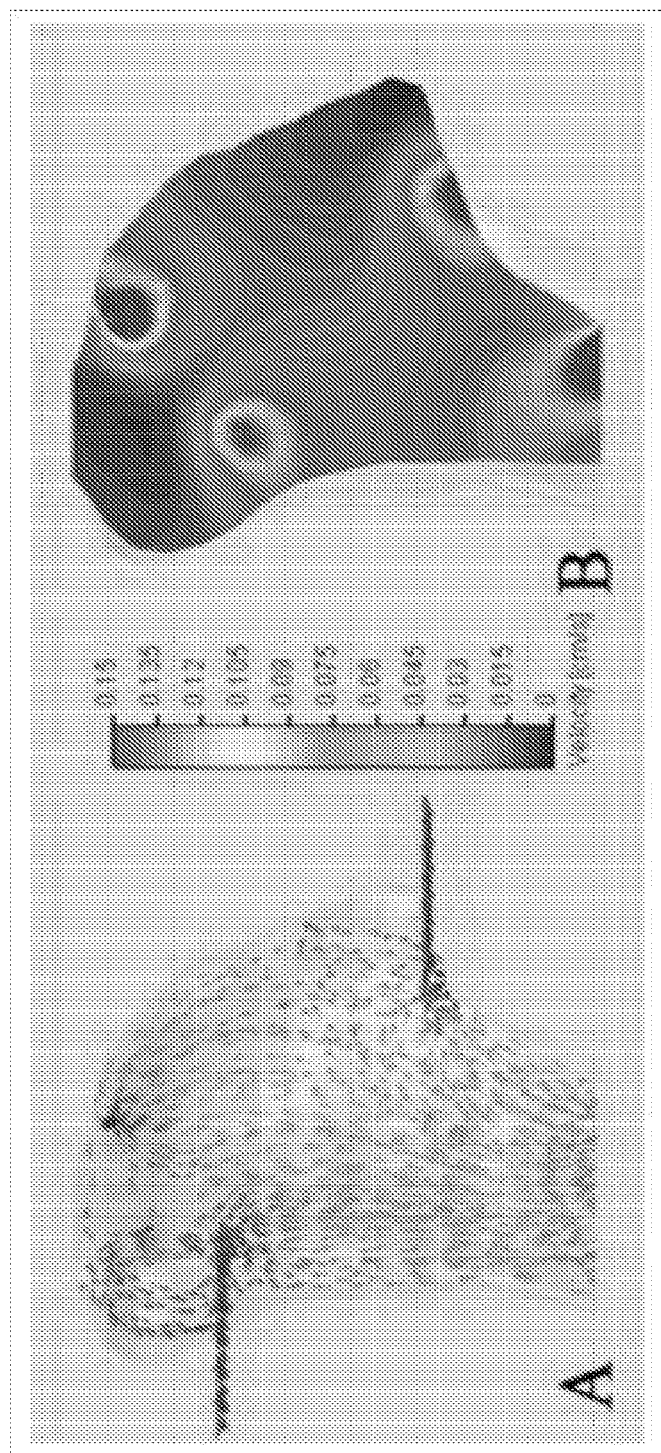
FIGS. 5A-5B show computational models of perfused flow in the bioreactor, according to one or more embodiments of the disclosed subject matter.

Computer-aided modeling can be performed to evaluate the effect of perfusion flow parameters. An example of such a computer model for a TMJ scaffold in the disclosed bioreactor is shown in FIGS. 5A-5B. In particular, theoretical modeling of the flow in the scaffold indicated a wide distribution in the magnitude (0 to 0.15 cm/s) and directions of flow velocities within the constructs. The flow rates were highest in the inlet and outlet regions, adjacent to the needle ports. Due to the complex geometry of the scaffold, its flat base is not at the center of the chamber, resulting in spatial gradients of flow distribution across the base. The lowest flow rates occurred at far-right and far-left projections of the scaffolds with the velocity vector computation indicating near zero flow at the extremities (FIG. 5A), since the outlet needle was not placed at the tip of the projection. Dye studies showed that medium does in fact perfuse these extreme regions. Histological analysis of 5-week scaffolds clearly demonstrated cell survival and matrix production in these regions.

Figures 5E, 5F:
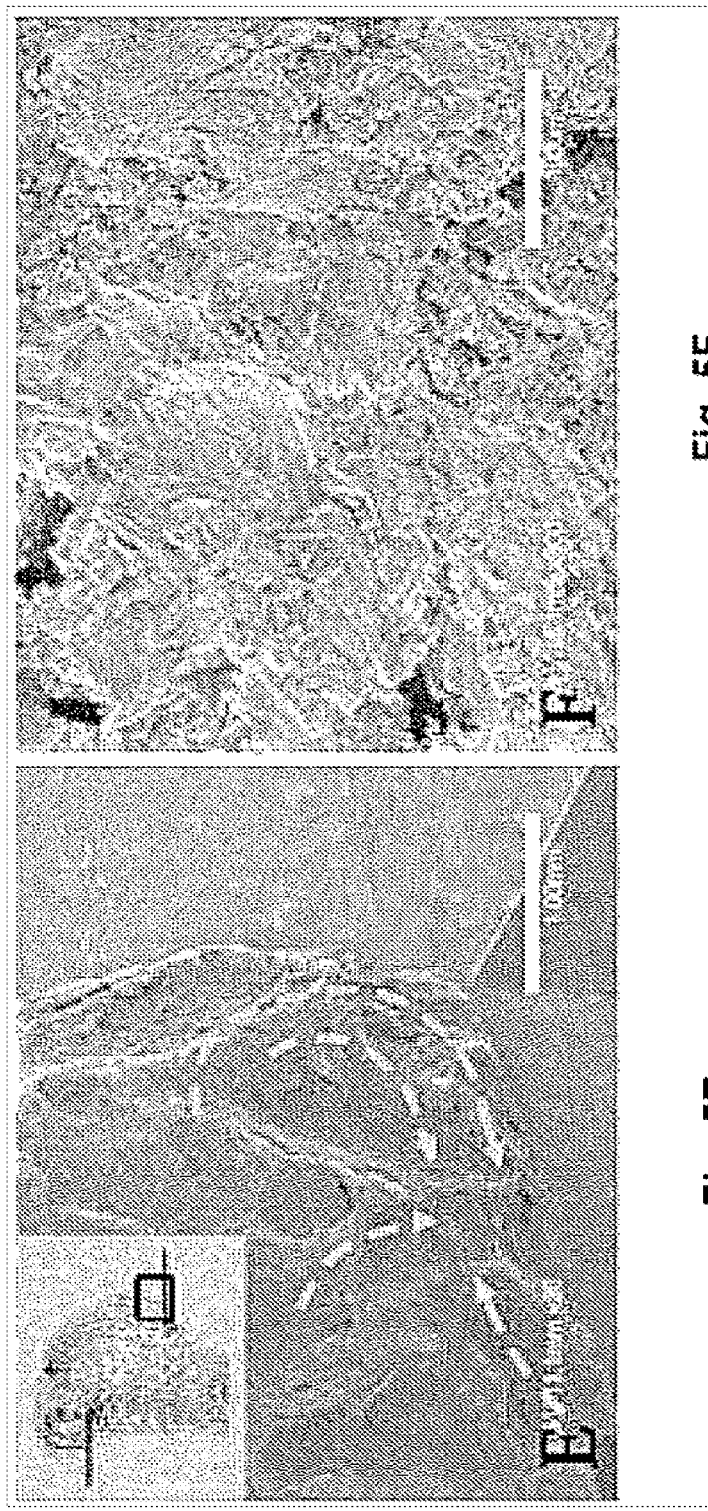

Referring now to FIGS. 5A-5F, bone matrix morphology has been correlated to the patterns of medium perfusion flow. FIG. 5A shows color-coded velocity vectors indicating the magnitude and direction of flow through the entire scaffold based on experimentally measured parameters. FIG. 5B is digitally sectioned, and the color-coded contours are used to indicate the magnitude of flow in the inner regions. Scanning electron microscopy (SEM) images demonstrated morphological variations in the tissue morphology with the variation in fluid flow pattern. For example, in the middle regions where the fluid flow is unidirectional, tissue appears smooth and aligned, and the crystalline structures can be easily seen on the surface (FIGS. 5C-5D). At the base of the projection, close to the outlet port, the model indicates large local changes in the velocity vector, effectively resulting in swirling flow patterns. High magnification SEM images of this region demonstrated a corresponding "swirling" of mineralized matrix structure (FIGS. 5E, F).

Thus, the approach disclosed herein demonstrates that it is possible to create bone grafts using a bioreactor that (i) houses anatomically shaped tissue scaffolds with complex geometries, (ii) provides controlled interstitial flow of culture media through the pore spaces of the scaffolds, and (iii)

enables the establishment of cultivation protocols for engineering large human bone grafts.

In embodiments, several tissue engineering operations may be employed including, but not limited to: (i) imaging guided fabrication of anatomical scaffolds; (ii) use of decellularized bone as an osteo-inductive scaffold; (iii) use of multi-potent mesenchymal stem cell populations, applicable in either autologous or allogeneic fashion; (iv) perfusion based environmental control and biophysical stimulation of cultured bone constructs; and (v) a computational modeling optimization of bioreactor design.

In embodiments, a method for bone tissue engineering can include, separately or in combination: (i) imaging at least a portion of a patient for a desired bone graft; (ii) machining a porous scaffold into the shape of the desired bone graft; (iii) seeding the porous scaffold with hMSCs; and (iv) perfusing culture medium throughout an interstitial volume of the porous scaffold for a period of time such that the hMSCs develop lamellae of bone tissue which fill the pore spaces of the scaffold.

The methods, systems, and devices for tissue engineering described herein thus enable the formation of geometrically complex bone constructs of high structural and biological fidelity. Computational modeling of fluid flow may also provide important insights into tissue responses to biophysical stimuli. Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting. In addition, although the production of bone tissue grafts have been specifically described herein, the techniques described herein are applicable to other tissues as well.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, methods, devices, and systems for bone tissue engineering using a bioreactor. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

What is claimed is:

1. A tissue engineering system comprising:
a porous scaffold matching a shape of a target anatomy of a patient that consists essentially of decellularized bone and is disposed within a three-dimensional vessel with an internal surface; wherein the internal surface of the three-dimensional vessel conforms to the shape of the scaffold;
a bioreactor having a recess configured to receive said vessel and a combination of inlet and outlet ports totaling at least three ports that is configured to accept at least one lumen and wherein the ports are placed to permit flow communication between the at least one lumen and an internal volume defined by the internal surface of said vessel;
wherein the three-dimensional vessel is disposed within the recess of the bioreactor; and
a flow mechanism configured to: introduce a perfusate into the recess of the bioreactor via the at least one inlet port; provide at least two different fluid flow rates; and circulate the perfusate between the at least one lumen and the internal volume of the vessel; and
wherein placement of the combination of inlet ports and outlet ports are determined by computer-aided modeling and establish a pattern that distributes perfusate throughout said scaffold.

2. The system of claim 1, wherein the vessel internal surface is configured to correspond to the target anatomy of the patient.

3. The system of claim 1, wherein the flow mechanism includes a pump.

4. The system of claim 1, wherein there is more than one inlet port.

5. The system of claim 4, wherein the inlet ports are configured to provide different fluid flow rates.

6. The system of claim 1, wherein the flow mechanism is configured to cycle between different flow rates.

7. The system of claim 1, wherein the flow mechanism is configured to apply a pressure differential to force the fluid to perfuse the scaffold.

8. The system of claim 1, wherein the flow mechanism provides a flow pattern associated with the scaffold shape.

9. The system of claim 1, wherein the combination of inlet ports and outlet ports is configured to introduce perfusate directly into the scaffold body at multiple points about the scaffold body such that an architecture of forming bone correlates to interstitial flow characteristics.

10. The system of claim 1, configured to produce a flow rate of at least 0.4 ml/minute.

11. The system of claim 1, wherein the combination of inlet ports and outlet ports is configured in a pattern that distributes perfusate through multiple surface portions of the scaffold and out through at least one second surface of the scaffold, and further wherein at least one second surface portion is determined responsively to a three-dimensional flow model of the scaffold.

12. The system of claim 1, wherein the perfusate includes cells.

13. The system of claim 1, wherein the scaffold is seeded with stem cells.

14. The system of claim 12, wherein the cells are derived from the patient.

15. The system of claim 13, wherein the stem cells are derived from the patient.

16. The system of claim 9, wherein the perfusate includes cells.

17. The system of claim 9, wherein the scaffold is seeded with stem cells.

18. The system of claim 16, wherein the cells are derived from the patient.

19. The system of claim 17, wherein the stem cells are derived from the patient.

* * * * *